US009651470B2

United States Patent
Hayden et al.

(10) Patent No.: US 9,651,470 B2
(45) Date of Patent: May 16, 2017

(54) FLUIDIC CELL GUIDANCE FOR FLOW CYTOMETRY

(75) Inventors: Oliver Hayden, Herzogenaurach (DE); Michael Johannes Helou, Regensburg (DE); Sandro Francesco Tedde, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 37 days.

(21) Appl. No.: 14/235,449

(22) PCT Filed: Jul. 24, 2012

(86) PCT No.: PCT/EP2012/064470
§ 371 (c)(1),
(2), (4) Date: Jan. 27, 2014

(87) PCT Pub. No.: WO2013/014146
PCT Pub. Date: Jan. 31, 2013

(65) Prior Publication Data
US 2014/0159714 A1 Jun. 12, 2014

(30) Foreign Application Priority Data
Jul. 28, 2011 (DE) .................. 10 2011 080 012

(51) Int. Cl.
*G01N 33/543* (2006.01)
*G01N 33/553* (2006.01)
(Continued)

(52) U.S. Cl.
CPC .... *G01N 15/1031* (2013.01); *B01L 3/502746* (2013.01); *B01L 3/502761* (2013.01);
(Continued)

(58) Field of Classification Search
CPC .......... G01N 27/745; G01N 33/54326; G01N 33/54333; G01N 33/553; G01N 2015/1081
(Continued)

(56) References Cited

U.S. PATENT DOCUMENTS 6,736,978 B1 * 5/2004 Porter et al. .................. 210/695
7,179,383 B1 2/2007 Porter et al.
(Continued)

FOREIGN PATENT DOCUMENTS

| CN | 1650162 A | 8/2005 | |
|---|---|---|---|
| WO | WO2009132151 | * 10/2009 | ............... B01L 3/00 |
| WO | WO2009132151 A2 | 10/2009 | |

OTHER PUBLICATIONS

"Principle of flow cytometry"; Acta Acad Med Nei Mongol; vol. 24, No. 3, pp. 203-207; 2002.
(Continued)

*Primary Examiner* — Son Le
*Assistant Examiner* — Neel Shah
(74) *Attorney, Agent, or Firm* — Lempia Summerfield Katz LLC

(57) ABSTRACT

The invention relates to a device and a method for fluidic cell guidance for flow cytometry or analyte enrichment. This allows magnetically marked analytes, in particular cells (1), to be dynamically enriched and individually detected in the flow from a sample, in particular magnetoresistively. For cell guidance, guiding ridges (12) are arranged in a flow channel (100), and so, in addition to a magnetic enrichment force ($10_z$) and the shearing force of the flow ($10_y$), a deflecting force ($10_x$) caused by the fluidic obstacles (12) also acts on the cells (1) to be detected.

18 Claims, 6 Drawing Sheets

(51) Int. Cl.
*G01N 15/10* (2006.01)
*B01L 3/00* (2006.01)

(52) U.S. Cl.
CPC . *B01L 3/502776* (2013.01); *B01L 2300/0816* (2013.01); *B01L 2400/043* (2013.01); *B01L 2400/086* (2013.01)

(58) Field of Classification Search
USPC ............ 324/204, 207.21; 436/149, 150, 526, 436/806; 210/222, 223, 265
See application file for complete search history.

(56) References Cited

U.S. PATENT DOCUMENTS

| | | | |
|---|---|---|---|
| 9,220,831 B2* | 12/2015 | Ingber | A61M 1/36 |
| 2003/0095897 A1 | 5/2003 | Grate et al. | |
| 2008/0124779 A1* | 5/2008 | Oh et al. | 435/173.9 |
| 2008/0160630 A1* | 7/2008 | Liu et al. | 436/164 |
| 2009/0208372 A1 | 8/2009 | Mott et al. | |
| 2010/0044232 A1* | 2/2010 | Lin et al. | 204/660 |
| 2011/0003303 A1 | 1/2011 | Pagano et al. | |
| 2011/0059500 A1 | 3/2011 | Wo et al. | |
| 2014/0159714 A1 | 6/2014 | Hayden et al. | |
| 2014/0251879 A1* | 9/2014 | Deshpande | B07C 5/02 209/577 |

OTHER PUBLICATIONS

Chinese Office Action for German Application No. 2012 80 0377 48.8 mailed Jun. 9, 2011, with English Translation.
German Office Action for German Application No. 10 2011 080 012.3, mailed Apr. 18, 2012, with English Translation.
Howell, Peter B., Jr., et al., "Two Simple and Rugged Designs for Creating Microfluidic Sheath Flow," The Royal Society of Chemistry, 8, pp. 1097-1103, 2008.
PCT International Search Report and Written Opinion of the International Searching Authority dated Dec. 3, 2012 for corresponding PCT/EP2012/064470.

* cited by examiner

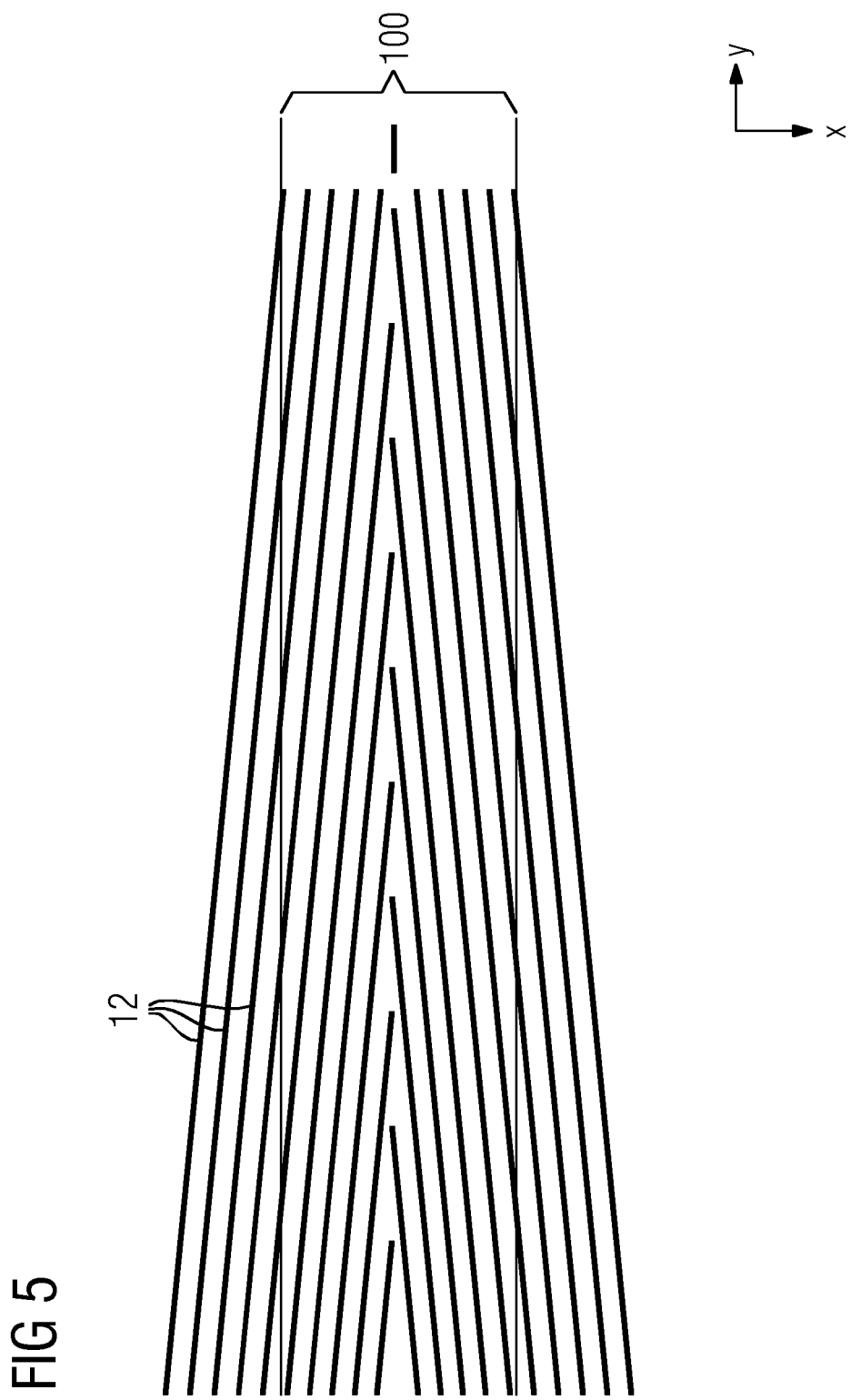

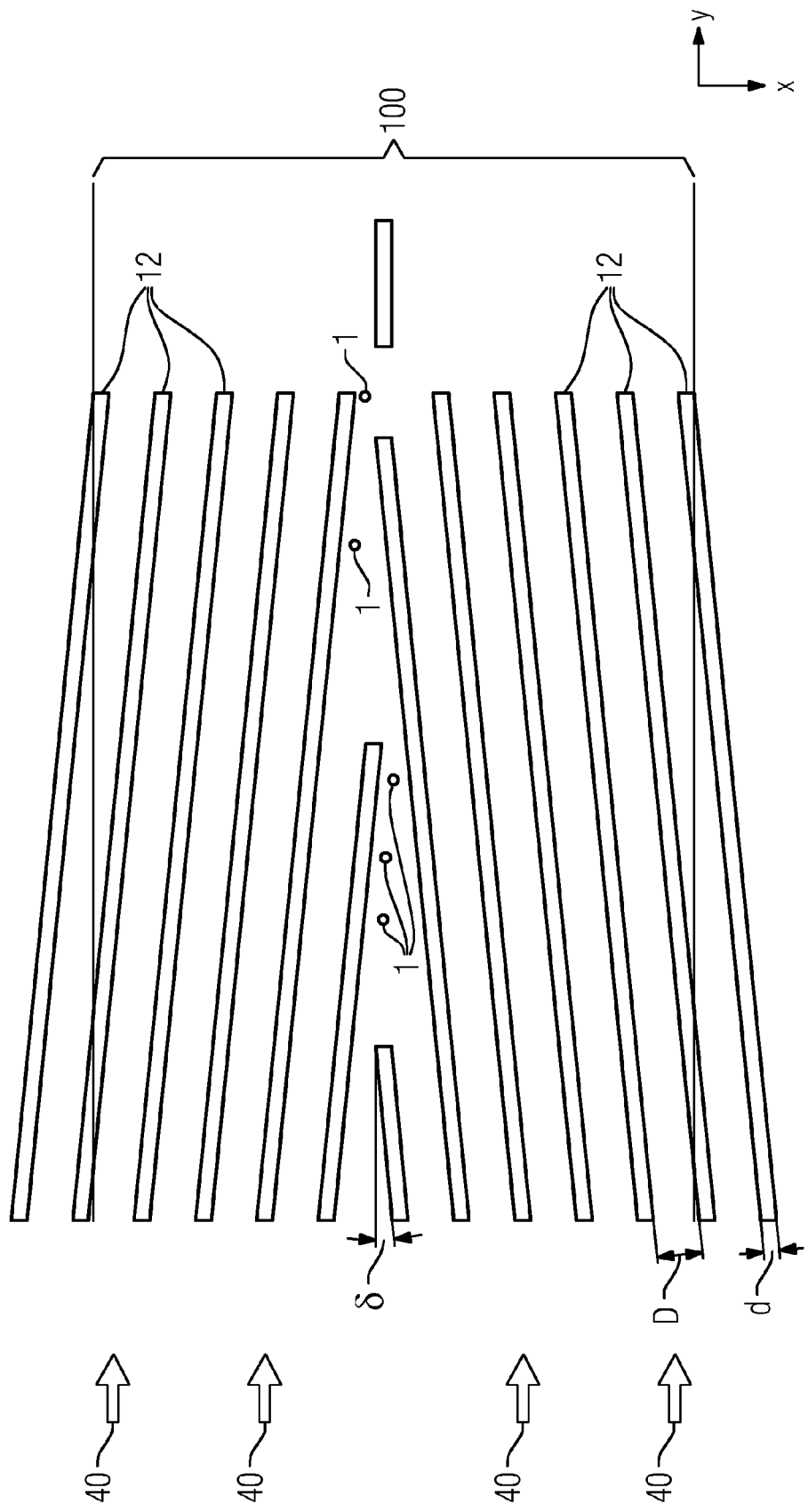

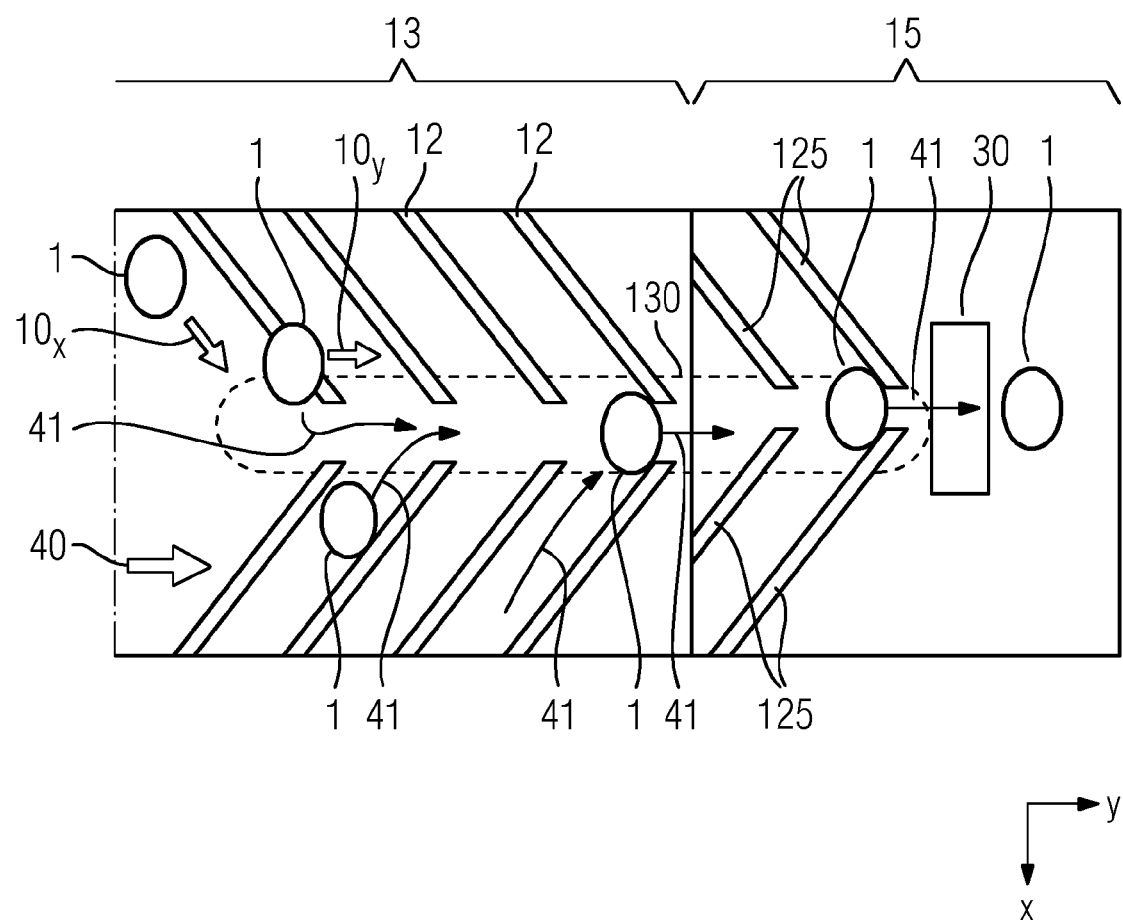

FLUIDIC CELL GUIDANCE FOR FLOW CYTOMETRY

The present patent document is a §371 nationalization of PCT Application Serial Number PCT/EP2012/064470, filed Jul. 24, 2012, designating the United States, which is hereby incorporated by reference. This patent document also claims the benefit of DE 10 2011 080 012.3, filed Jul. 28, 2011, which is also hereby incorporated by reference.

BACKGROUND

The present embodiments relate to flow cytometry.

In the field of cell measurement and cell detection, optical measurement methods, such as scattered-light or fluorescence measurement, and magnetic detection methods are known.

In magnetic detection methods, for example, for cell sorting, cell guidance or cell enrichment, magnetophoresis, in which a magnetic force is exerted on the marked cells by magnetic guide strips, such that these cells may be separated or also aligned with a cell measuring device following these guide strips, is known. To date, with the aid of a gradient magnetic field, enrichment of marked cells or particles has been carried out on a substrate surface on which the cells or particles to be detected are aligned by magnetophoresis.

In order to produce such a magnetophoretic enrichment and alignment section, it is known to apply magnetic strips onto the substrate (e.g., by lithography). Such production methods, however, are very elaborate and therefore disadvantageous for the production of a component that is intended for large production numbers. A further disadvantage of the magnetophoretic enrichment section is that the silicon footprint thereby increased. For the integration of an enrichment section and cell measuring device on a silicon chip, the size of the silicon chip exceeds reasonable costs for the use of such components.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a more simply producible apparatus for flow cytometry is provided.

The apparatus according to one or more of the present embodiments for flow cytometry includes a flow channel, a magnetic unit that is arranged below the channel bottom of the flow channel and is configured to generate a gradient magnetic field that permeates the volume enclosed by the flow channel, at least one cell measuring device, and at least one guide step. The at least one guide step is arranged in the flow channel such that cells that may flow through the flow channel may be deflected toward the at least one cell measuring device by the at least one guide step. This has the advantage that the cells to be detected in a microfluidic system may be enriched in two dimensions by the flow conditions and the gradient magnetic field. The apparatus also has the advantage of being able to obviate magnetophoretic enrichment and therefore of being structurally much less elaborate than previously known enrichment sections.

In one embodiment, the apparatus includes a flow channel that is configured with respect to channel diameter and surface condition of the inner wall of the channel such that a flow of a complex cell suspension in the flow channel may be generated with a laminar flow profile. For example, the flow channel is a microfluidic channel. Operation may be carried out with relatively large channel diameters that provide laminar flow of a complex solution without obstructions occurring (e.g., due to deposits). The configuration of the channel with the guide step also provides enrichment in the direction of the cell measuring device. A Y-shaped microfluidic system such as is used, for example, for the separation of marked cells in the prior art is thus obviated.

In another embodiment, the apparatus includes a magnetic unit configured to generate a gradient magnetic field by which magnetically marked cells may be enriched on the channel bottom. The marking of the cells is, for example, superparamagnetic marking (e.g., using superparamagnetic beads). This has the advantage that all magnetically marked cells may be enriched on the channel bottom, where the magnetically marked cells are brought in the laminar flow to the at least one guide step, so that the magnetically marked cells may be deflected by the at least one guide step. In this case, the guide step has a height of about the cell diameter of the cell type to be detected.

The guide step in the apparatus is, for example, an elevation relative to the channel bottom or is formed from a depression relative to the channel bottom. In other words, the guide step forms, for example, a narrowing of the channel by extending as an elevation into the channel volume, or the guide step forms a widening of the channel by being formed as the edge of a depression (e.g., a trough) in the channel bottom. By virtue of these guide step embodiments, different fluid-mechanical influences may be exerted on the cell sample.

In the case of elevations relative to the channel bottom, the step height is the height of the elevation, and in the case of a depression relative to the channel bottom, the step height is the depth of the trough in the channel bottom. In this case, the trough outer wall, onto which the flow runs, forms the guide step.

For example, the apparatus includes a plurality of guide steps. The plurality of guide steps are arranged in the flow channel such that cells that may flow through the flow channel may be enriched by the plurality of guide steps in a subvolume of the flow channel over a subsurface of the channel bottom. This has the advantage that the apparatus does not involve a Y-shaped microfluidic system in which marked cells are sorted, but instead enrichment of the cells to be detected may be provided within the sample volume. In one embodiment, the subvolume or the subsurface of the channel bottom lies in the middle of the flow channel, toward which the cells may be enriched from both sides. For example, the cell measuring device is also arranged within the subsurface of the channel bottom. The cell measuring device is, for example, arranged on or in the channel bottom. For example, the detection region of the cell measuring device extends beyond the subvolume above the cell measuring device.

The elevations of the guide steps are, for example, configured such that the cells may not become stuck in intermediate spaces between the guide steps, and may not obstruct the intermediate spaces. The structure height (e.g., the height of the steps relative to the channel bottom) may therefore be of the order of the cell diameter (e.g., slightly less than the cell diameter). The arrangement of a plurality of guide steps is to leave free a sufficiently large subregion of the channel bottom, on which the enriched cells may continue on their way through the flow channel. Either a sufficiently wide channel is kept free between the guide steps or, as an alternative, a sufficient offset is provided in the case of finger structures.

In one exemplary embodiment of the apparatus, the guide steps may be formed by photoresist strips (e.g., on a silicon wafer). The photoresist steps are generated, for example, by photolithography.

The enrichment section is formed as a unitary plastic part with the guide steps (e.g., using injection molding), so that the enrichment section does not occupy any silicon substrate. This has the advantage of reducing the silicon footprint and therefore the production and component costs of the flow cytometry apparatus.

In one exemplary configuration, the guide steps of the apparatus extend over the channel bottom such that magnetically marked cells that experience a magnetic force in the direction of the channel bottom and a fluidic shear force in the flow direction may cross the guide steps only on a path over a predeterminable subsurface of the channel bottom. In other words, the guide steps meet, for example, with the channel walls on both sides of the channel bottom such that magnetically marked cells enriched on the channel bottom may not flow along the channel walls. For example, the guide steps extend over both longitudinal halves of the channel bottom, respectively, from one channel wall approximately as far as the middle of the channel. A passage for cells enriched on the channel bottom is provided in the flow direction. In this case, the guide steps may, for example, be arranged such that the subsurface over which the marked cells are enriched is a narrow rectangular subsurface that extends along the middle of the channel in the flow direction. As an alternative, the guide steps may also engage in one another in the manner of fingers, so that the subsurface over which the cells are enriched represents a subsection extending in a zigzag or in the shape of a wave. For example, the subsurface in the direction of which the cells are enriched may also taper in the course of the flow channel in the flow direction.

In one embodiment, the guide steps are configured integrally with the channel bottom. For example, the guide steps may be configured with the channel bottom as an injection-molded part. The embodiment as an injection-molded part has the advantage that, for the cell measurement, the enrichment section may not be arranged on the substrate (e.g., a silicon wafer). In this way, the footprint (e.g., the size of the silicon substrate) for the flow cytometry component may be reduced considerably, which also reduces the cost of such a flow cytometry apparatus. Furthermore, the configuration of the fluid-mechanical enrichment section is substantially simpler to produce (e.g., compared with lithographic methods such as are used in the production of magnetophoretic enrichment sections).

For example, the guide steps are straight linear elevations relative to the channel bottom. With the straight linear shape, the cells enriched on the bottom are transported by the laminar flow along the steps without perturbing turbulence occurring in the flow at the channel bottom. As an alternative, the guide steps may extend in a curve in the direction of the middle of the channel. For the orientation of the straight linear steps, these are, for example, arranged at an acute angle with respect to the flow direction. In other words, the enriched cells that are to be transported along the guide steps are not held back by the guide steps, but rather, the transport of the cells continues in the flow direction.

The apparatus with the enrichment section includes a combination of guide steps on a separate plastic channel segment. The guide steps may, for example, be configured integrally with the channel bottom and a small part of the enrichment section using photoresist steps on the silicon wafer, on which the cell measuring device is also arranged. By such a combination, the silicon footprint may be reduced. The cells are enriched on an enrichment section of any desired length by the geometry of the guide steps and the fluid-mechanical conditions, and as soon as the cells reach the silicon wafer, the cells are also enriched at the silicon wafer before the cell measuring device, which may also be preceded by a few (e.g., two or more) guide steps, in order to maintain the enrichment and alignment of the cells when passing over the new channel bottom substrate.

The hybrid form of the enrichment section thus forms an advantageous variant for reducing the silicon footprint. The structure of the fluid-mechanical enrichment section by the guide steps on a plastic substrate then, for example, precedes the silicon die. For example, the magnetoresistive components for detection of the magnetically marked individual cells lie on the silicon die.

A hybrid enrichment section of this type may, for example, also include a part in which the guide steps contain a proportion of nickel or are produced as nickel strips. With a proportion of nickel in the guide steps, excess unbound magnetic markers may be retained by magnetic holding forces on the nickel strips or nickel guide steps, and may be filtered out of the complex suspension. For example, nickel guide steps are structured using laser ablation. For example, the guide steps with a proportion of nickel precede the enrichment section with the guide steps not containing nickel (e.g., the guide steps with a proportion of nickel are arranged before the guide steps in the flow direction in the channel). As an alternative, however, the guide and filter strips containing nickel may also be arranged on the silicon substrate immediately before reaching the cell measuring device. The guide and filter strips containing nickel thus fulfill the double function of enrichment and guidance as well as filtering of excess markers.

The dynamic enrichment and cell guidance in the flow provides the advantage of the apparatus that enrichment and measurement may be carried out in one channel. The apparatus is not intended for sorting using Y-shaped separation of marked cells from the surrounding complex suspension. Excess markers do not have to be separated elaborately from the suspension, but may be retained by the guide steps. For example, the guide steps are arranged in terms of height and angle of the guide steps with respect to the flow direction such that unbound magnetic markers, which are much smaller in terms of hydrodynamic diameter than marked cells, remain on the guide steps and are held back (e.g., may not cross the steps). Only the larger fractions or particles, such as marked cells in the complex suspension, are entrained in the laminar flow and are thus transported along the steps. Nonmagnetic or nonmagnetophoretic enrichment (e.g., using the guide steps) may also exert a filter effect on excess and therefore undesired markers in the measurement region of the cell measuring device.

In order to reinforce the fluid-mechanical filter effect at the guide steps, which, for example, are nonmagnetic (e.g., do not contain a proportion of nickel), the guide steps may be varied in terms of height (e.g., adapted to the size of the cell type to be detected and the size of the unbound magnetic particles, or markers, to be filtered). In one embodiment, the step height increases in the course of the flow channel in the flow direction. The first step is still very low and may be crossed by most particles and cells. In the course of the channel, the step height then rises increasingly and thus retains larger and larger particles. Only the magnetically marked cells that are intended to be detected are not stopped by the steps, but are transported along the steps and concentrated in a subvolume of the channel. All steps point, for example, toward this subvolume, which lies, for example, in the middle of the channel on the channel bottom.

The channel diameter or the channel height and width are, for example, a few hundred μm (e.g., 200 μm). The step height is dependent on the cell type to be detected and the cell diameter thereof, and is, for example, a few micrometers (e.g., 10 μm or up to 30 μm). The flow channel may thus, for example, guide a sufficiently large volume of a complex suspension without thereby being obstructed.

In the method according to one or more of the present embodiments for magnetic flow cytometry, a laminar flow of a cell sample is generated, and the cells are enriched by guide steps in a predeterminable subvolume of the flow channel. In this case, the cells to be detected are magnetically marked and are dynamically enriched on the channel bottom in a gradient magnetic field. This method has the advantage that fluid-mechanical and magnetic forces interact such that magnetically marked cells may be enriched in a controlled manner in a predeterminable volume without needing to be separated from the cell suspension. In one embodiment of the method, the subvolume extends in the flow direction along the channel bottom, so that the cells are guided along an axis individually over a cell measuring device.

For the flow cytometry method, for example, a blood sample is transported in a laminar fashion through the microfluidic system. In the flow, the cells are partially aligned close to the channel bottom by the structuring of the substrate (e.g., the guide steps). In the gradient field, for example, superparamagnetic analytes are drawn onto the structured channel bottom and detected at the structured channel bottom magnetoresistively.

In the method for magnetic flow cytometry, three forces thus act on the magnetically marked cells or on magnetic beads, or generally on magnetic particles to be detected. A magnetic force of the gradient magnetic field that is generated by the magnetic unit below the channel bottom is a first force of the three forces. Magnetic field strengths of this gradient field are, for example, between 1 and 300 mT. This magnetic force thus attracts the cells perpendicularly toward the channel bottom surface. A shear force of the flowing cell sample acts on the individual cells as a second of the three forces. The flow is, for example, a laminar flow. This force thus acts in the direction of the cell sample flow through the channel. A third force of the three forces is exerted by the guide steps on the channel bottom. The guide steps represent a fluid-mechanical obstacle for the magnetically marked cells enriched on the bottom. The effect of this is that, in order to proceed further in the flow direction, the cells move along the guide steps toward the middle of the channel or in general, depending on the orientation of the guide steps, toward a subregion of the channel. The magnetic marking may be carried out using superparamagnetic particles.

When the flow cytometry method is carried out, the flow rate, the surface property and the magnetic field strength also play a role. The flow rate, for example, is adapted to the cell sample and, above all, to the channel diameter in order to provide a laminar flow. Using surface functionalization, the surface properties of the channel inner walls and of the channel bottom may be optimized. Using the field strength of the gradient magnetic field, further influence may be exerted on the cells to be deflected and enriched. The cells to be detected also have mechanical properties that may be influenced by the values of the flow rate, surface condition and magnetic field strength.

In the production method according to one or more of the present embodiments for an apparatus for flow cytometry, guide steps are configured integrally with the channel bottom (e.g., as an injection-molded part).

The apparatus according to one or more of the present embodiments thus has the advantage of offering a solution for flow cytometry without magnetophoresis. For example, a substrate structured in this way, which correspondingly guides and enriches the magnetically marked cells by the guide steps (e.g., the structure of the substrate bottom) may be produced by various techniques (e.g., injection molding or embossing). Accordingly, no lithographic outlay such as in magnetophoretic enrichment is necessary. The magnetic guide lines of a magnetophoretic enrichment section are replaced by a three-dimensional structure of the substrate bottom. For example, the herringbone shape is adopted in this case. The structuring has, for example, linear elevations that are referred to as guide steps. These are arranged, for example, at a steep angle to the flow direction through the channel. The steps may measure heights of between 0.1 and 20 μm relative to the channel bottom. In width, the guide steps measure between 1 and 100 μm, for example. The length of the guide steps is selected as a function of the channel width such that the guide steps end at the channel edge with the channel wall, and reach approximately to the middle of the channel. Either the guide steps reach only almost as far as the middle, so that a passage between the guide steps that extend from both sides in the direction of the middle of the channel remains, or as an alternative, the guide steps extend in terms of length beyond the middle of the channel and are then arranged engaging in one another in the manner of fingers. The angle with respect to the flow direction is, for example, less than 45° (e.g., less than 20°).

In the flow cytometry method, for example, a blood sample is transported in a laminar fashion through the microfluidic system. Cells within this blood sample are partially aligned close to the substrate surface by the substrate structuring. Magnetically marked analytes (e.g., superparamagnetically marked analytes) are attracted in the gradient field onto the substrate surface (e.g., onto the channel bottom) and are guided close to the substrate (e.g., on the channel bottom), where the substrate structuring may influence the magnetically marked analytes. The cells enriched and aligned in this way may then be detected magnetoresistively.

BRIEF DESCRIPTION OF THE DRAWINGS

FIG. 5 shows another plan view of another embodiment of an arrangement with the guide troughs or steps arranged in a herringbone fashion;

FIG. 6 shows an enlarged detail of FIG. 4; and

FIG. 7 shows an exemplary hybrid cell enrichment section.

DETAILED DESCRIPTION

Figure 1:
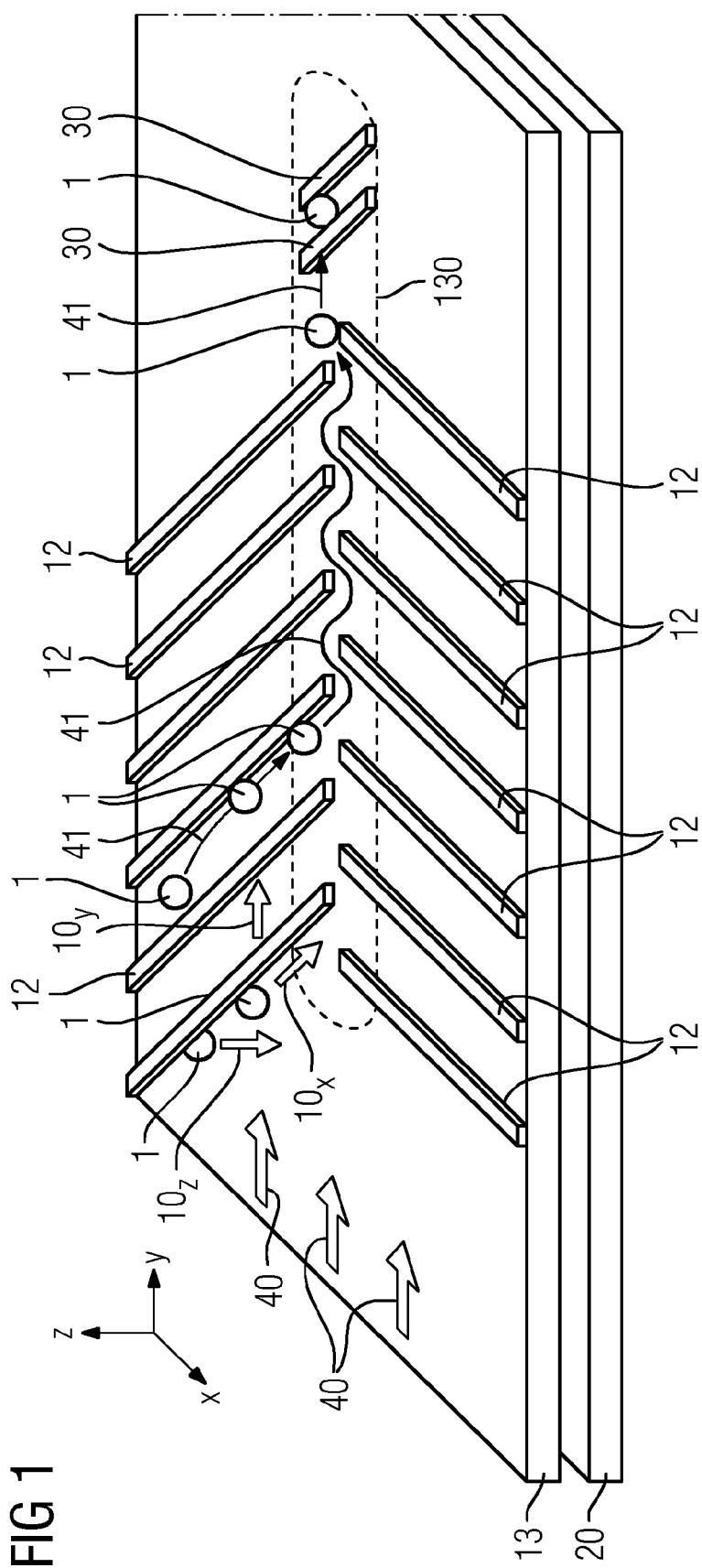
FIG. 1 shows a perspective view of one embodiment of a channel bottom with cell-guiding elevations.

FIG. 1 shows a perspective view of an exemplary channel bottom 13 that is represented as a flat substrate. At a distance thereunder, a further flat cuboid 20 is shown. The further flat cuboid 20 represents the magnetic unit 20. The magnetic unit is, for example, a permanent magnet. The magnetic unit 20 may also extend over an area larger than an area of the channel bottom 13 in order to provide a homogeneous magnetic field in the region of the flow channel 100. For example, the magnetic unit 20 generates in the flow channel 100 a gradient field in which magnetic particles (e.g., the magnetically marked cells 1 or unbound magnetic markers) are enriched in the negative z direction toward the channel bottom 13. The x, y and z directions are respectively indicated by small coordinate systems at the edge in the figures. In FIG. 1, a plurality of guide steps 12 (e.g., elevations) that are represented as narrow cuboids are arranged on the channel bottom substrate 13. These elevations or guide steps 12 meet (e.g., an edge of the channel bottom 13 or channel walls 14). The channel walls 14 are not shown in the representation of FIG. 1. The guide steps 12 project into the middle of the flow channel 100. The guide steps 12 do not join with opposite guide steps at the middle of the flow channel 100. The guide steps 12 either leave a straight passage in the middle or engage in one another in the manner of fingers such that a zigzag or serpentine line may extend through the guide steps 12. In one embodiment, flow paths of magnetically marked cells 1 are indicated by arrows 41 in FIG. 1. The magnetically marked cells 1 are shown as circles or ovals. The forces $10_{x,y,z}$ acting on the cells are indicated by double arrows. Wide double arrows indicate the flow direction 40, which extends from left to right in FIG. 1. In the flow channel 100, the magnetically marked cells 1 are thus introduced at one end within a complex cell suspension and flow in the flow direction 40 through the enrichment section with the guide steps 12. Owing to the magnetic force $10_z$, which points in the direction of the channel bottom 13, owing to the shear force 10 of the liquid in laminar flow, which points in the flow direction 40, and owing to the guide steps 12 that represent a barrier, which in turn exert a mechanical force $10_x$ in the x-y plane of FIG. 1 on the cells 1, the cells 1 are displaced along the guide steps in the direction of a subregion 130 of the channel bottom 13. At the end of the subregion 130, in which the cells 1 are concentrated, a cell measuring device 30 that, for example, includes at least one magnetoresistive element is provided.

Figure 2:
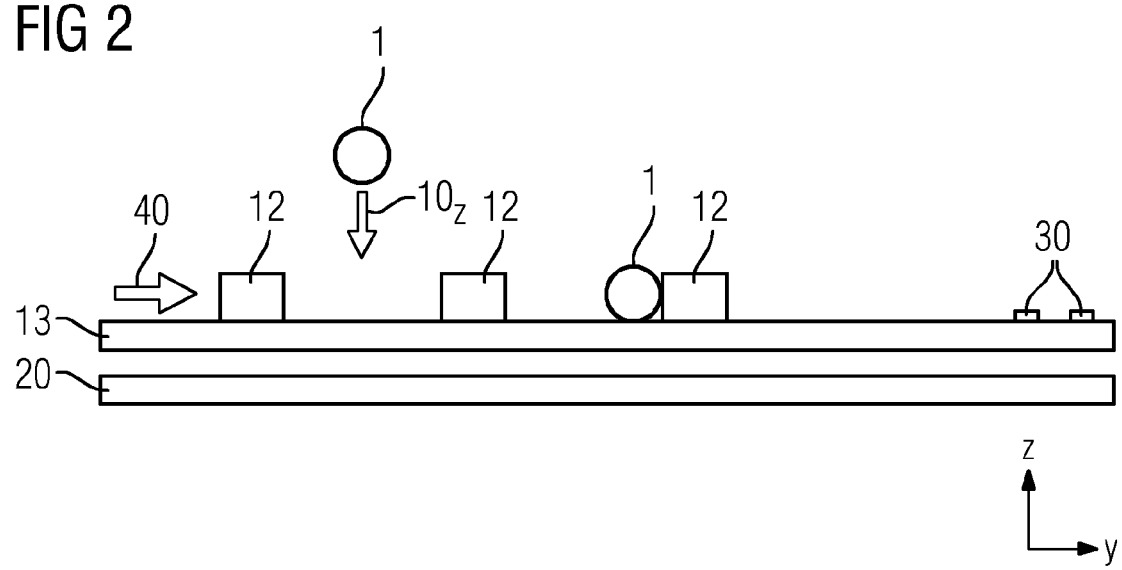
FIG. 2 shows a side view of one embodiment of the channel bottom with underlying permanent magnets.

FIG. 2 shows a side view of one embodiment of an apparatus similar to the apparatus in FIG. 1. In this case, two flat rectangles that represent the substrate or the channel bottom 13, and at a distance thereunder, the magnetic unit 20, are arranged above one another. As an alternative to the embodiment shown, the permanent magnet may also be arranged directly below the channel bottom 13 without a separation. Above the channel bottom 13, the flow direction 40, in FIG. 2 from left to right, is indicated by a double arrow, and a cross section through three of the guide steps 12 as well as through the cell measuring device 30 is shown at the right-side of FIG. 2, and therefore at the end of the enrichment section. Due to the permanent magnet 20, the magnetically marked cells 1 experience a magnetic force 10 perpendicularly in the direction of the channel bottom 13. The height of the guide steps 12 is, for example, adapted to the extent (e.g., the hydrodynamic diameter) of the magnetically marked cells 1, and is, for example, slightly less than the cell diameter. With a height that is too low, however, the magnetically marked cells would not experience any guide force 10 due to the steps 12, but would be carried away over the guide steps 12 in the laminar flow. With excessively high barriers 12, the magnetically marked cells 1 may no longer experience any shear force $10_y$ due to the flow and may remain behind the guide steps 12.

Figure 3:
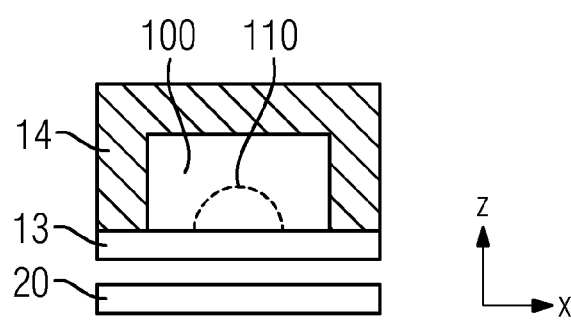
FIG. 3 shows a cross section of one embodiment of the flow channel.

FIG. 3 shows a cross section of one embodiment of the flow channel 100. In FIG. 3, the magnetic unit 20 and, at a distance thereover, the substrate 13 for the channel bottom 13 are shown as narrow rectangles. The channel wall 14 that encloses a cuboid channel volume is arranged thereover. In the flow channel 100, the subvolume 110 in which the magnetically marked cells 1 are enriched is also represented by dashes.

Figure 4:
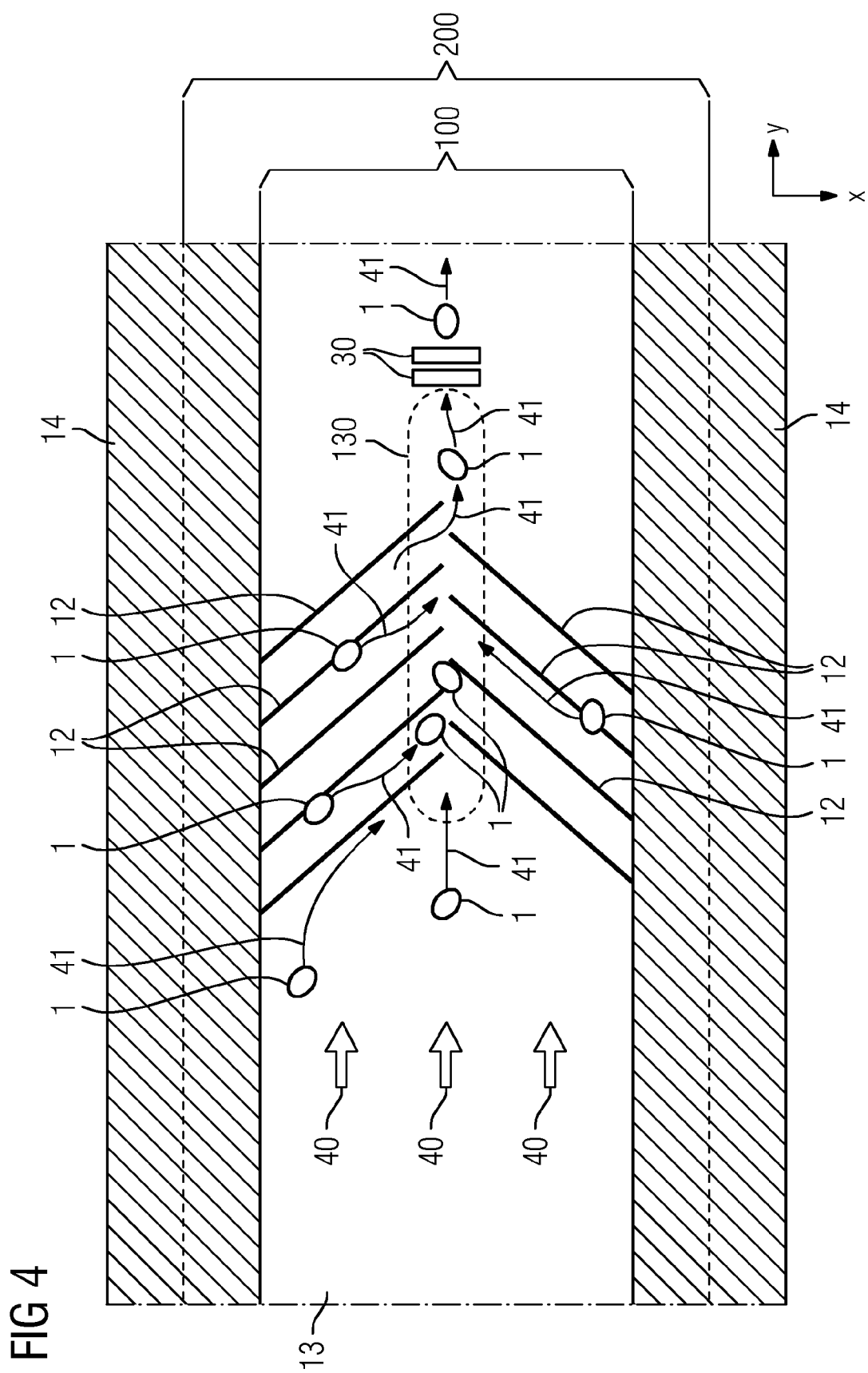
FIG. 4 shows a plan view of one embodiment of an arrangement with guide troughs or steps arranged in a herringbone fashion.

FIG. 4 shows a plan view of one embodiment of the channel bottom 13, on which the flow direction from left to right in FIG. 4 is again indicated by double arrows 40. Respectively at the side of the channel bottom 13, the channel walls 14 are represented in section by shading. A dashed line, which denotes the end of the magnetic region, respectively extends inside the channel walls 14. In other words, the distance between the dashed lines 200 shows the width of the region permeated by the magnetic field. The region permeated by the magnetic field is, for example, wider than the flow channel 100. This provides that the magnetic field in the channel volume is as homogeneous as possible. The region 200 permeated by the magnetic field is generated by the magnetic unit 20, which is arranged below the channel bottom 13, as shown in FIGS. 1 to 3. In the channel 100, guide steps 12 are arranged at an angle δ with respect to the channel wall 14, so that the guide steps 12 point from the channel wall 14 in the direction of the middle of the channel in the flow direction 40. The magnetically marked cells 1, as indicated by the flow paths 41, may thus be deflected at the guide steps 12 in the direction of the subregion 130, which extends as far as or beyond the cell measuring device 30.

FIG. 5 shows one embodiment of an arrangement of guide steps 12 that are arranged at an acute angle δ with respect to one another. The channel width 100 is again indicated. FIG. 6 shows an enlarged detail of FIG. 5 with guide steps 12, converging at an acute angle δ, that have a step thickness or width d and a distance D between the steps. The angle δ at which the steps 12 are arranged with respect to the flow direction 40 may, for example, be measured relative to the midline of the channel as shown in FIG. 6 or relative to the channel wall 14. Again, magnetically marked cells 1 are indicated as small circles in FIG. 6. It is illustrated that a sufficiently wide flow path through between the steps 12 is provided for the cells 1, so that the steps 12 do not obstruct the guide step intermediate spaces.

FIG. 7 shows another possible configuration of the apparatus, with a hybrid enrichment section. In the left-hand region of FIG. 7, the enrichment section is shown on a plastic substrate 13 with plastic guide steps 12, with which lead to the described fluid-mechanical enrichment of the cells 1. This is followed in the right-hand region of the drawing by the substrate 13 of the silicon chip 15, on which the cell measuring device 30 is arranged. This may, as shown in the example of FIG. 7, also have further guide steps 125 that, for example, continue the enrichment section onto the subregion 130.

The flow direction 40 is again represented by a double arrow from left to right in the drawing. The magnetically marked cells 1 are represented as ovals, and flow paths of the magnetically marked cells 1 are denoted by arrows 41. In the example shown in FIG. 7, the guide steps 12, which meet the channel walls 14 on both sides, do not engage in one another in the manner of fingers, but leave a straight flow region open in the region of the middle of the channel, which lies in the enrichment subregion 130. In order to guide the cells 1 straight over the cell measurement region 30 after the enrichment section through the guide steps 12, the silicon chip 15 also has a small portion of an enrichment section with guide steps 125. The guide steps 125 may, for example, also contain a proportion of nickel in the material of the guide steps 125 and therefore filter out still unbound markers by magnetic retaining forces before the cell measuring device 30. As an alternative, the guide steps 125 may be produced on the silicon chip 15 (e.g., by photoresist structures).

FIG. 7 again shows by double arrows the deflecting force $10_x$ that guides the cells 1 along the guide steps 12 to the middle, as well as the shear force $10_y$, of the fluid flow, which points in the flow direction 40.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus for flow cytometry, the apparatus comprising:
  a flow channel;
  a magnetic unit that is arranged below a channel bottom of the flow channel and is configured to generate a gradient magnetic field that permeates a volume enclosed by the flow channel;
  at least one cell measuring device; and
  at least one guide step that is arranged in the flow channel such that cells that are flowable through the flow channel are deflectable toward the at least one cell measuring device by the at least one guide step,
  wherein the at least one cell measuring device is arranged on or in the channel bottom,
  wherein the at least one guide step comprises a plurality of guide steps that are arranged in the flow channel such that the cells that are flowable through the flow channel are enrichable by the plurality of guide steps in a subvolume of the flow channel over a subsurface of the channel bottom, and
  wherein the plurality of guide steps extend away from the channel bottom of the flow channel such that the plurality of guide steps are barriers that exert mechanical forces on the cells that are flowable through the flow channel and a subset of the cells that are flowable through the flow channel do not flow over the plurality of guide steps.

2. The apparatus of claim 1, wherein the flow channel is configured with respect to channel diameter and surface condition of an inner wall of the flow channel such that a flow of a complex cell suspension in the flow channel is generatable with a laminar flow profile.

3. The apparatus of claim 2, wherein the magnetic unit is configured to generate a gradient magnetic field by which magnetically marked cells are enrichable on the channel bottom.

4. The apparatus of claim 2, wherein the at least one guide step is an elevation relative to the channel bottom or is formed from a depression relative to the channel bottom.

5. The apparatus of claim 2, wherein the at least one guide step comprises a plurality of guide steps that are arranged in the flow channel such that the cells that are flowable through the flow channel are enrichable by the plurality of guide steps in a subvolume of the flow channel over a subsurface of the channel bottom.

6. The apparatus of claim 2, wherein the at least one cell measuring device is arranged on or in the channel bottom.

7. The apparatus of claim 1, wherein the magnetic unit is configured to generate a gradient magnetic field by which magnetically marked cells are enrichable on the channel bottom.

8. The apparatus of claim 7, wherein superparamagnetically marked cells are enrichable by the gradient magnetic field on the channel bottom.

9. The apparatus of claim 1, wherein the at least one guide step is an elevation relative to the channel bottom or is formed from a depression relative to the channel bottom.

10. The apparatus of claim 1, wherein the plurality of guide steps extend over the channel bottom such that magnetically marked cells that experience a magnetic force in the direction of the channel bottom and a fluidic shear force in a flow direction are operable to cross the plurality of guide steps only on a path over a predeterminable subsurface of the channel bottom.

11. The apparatus of claim 1, wherein the plurality of guide steps are configured integrally with the channel bottom.

12. The apparatus of claim 11, wherein the plurality of guide steps are configured integrally with the channel bottom as an injection-molded part.

13. The apparatus of claim 1, wherein the plurality of guide steps are straight linear elevations relative to the channel bottom.

14. The apparatus of claim 1, wherein the plurality of guide steps are arranged at an acute angle with respect to a flow direction.

15. The apparatus of claim 14, wherein the plurality of guide steps are arranged in the flow channel, such that a serpentine path extends through the plurality of guide steps.

16. A method for magnetic flow cytometry, the method comprising:
  generating a laminar flow of a cell sample;
  magnetically marking cells; and
  dynamically enriching the cells on a channel bottom of a flow channel in a gradient magnetic field,
  wherein the cells are enriched in a predeterminable subvolume of the flow channel over a subsurface of the channel bottom using guide steps, the guide steps extending away from the channel bottom of the flow channel such that the guide steps are barriers that exert mechanical forces on the cells and a subset of the cells do not flow over the guide steps, and
  wherein the subsurface extends in a flow direction along the channel bottom, so that the cells are guided along an axis over a cell measuring device, the cell measuring device being arranged on or in the channel bottom.

17. A production method for an apparatus for flow cytometry, the apparatus comprising a flow channel, a magnetic unit that is arranged below a channel bottom of the flow channel and is configured to generate a gradient magnetic field that permeates a volume enclosed by the flow channel, at least one cell measuring device, and at least one guide step that is arranged in the flow channel such that cells that are flowable through the flow channel are deflectable toward the at least one cell measuring device by guide steps and a subset of the cells that are flowable through the flow channel do not flow over the at least one guide step, the at least one guide step being a barrier that exerts mechanical forces on the cells that are flowable through the flow channel, the at least one cell measuring device being arranged on or in the channel bottom, the method comprising:

configuring the guide steps integrally with the channel bottom such that the guide steps extend away from the channel bottom.

18. The production method of claim 17, wherein the configuring comprises configuring the guide steps integrally with the channel bottom as an injection molded part.

* * * * *